(12) United States Patent
Wong

(10) Patent No.: US 6,919,440 B2
(45) Date of Patent: Jul. 19, 2005

(54) MANNOSYL TRANSFER WITH REGENERATION OF GDP-MANNOSE

(75) Inventor: Chi-Huey Wong, Rancho Santa Fe, CA (US)

(73) Assignee: The Scripps Research Institute, La Jolla, CA (US)

( * ) Notice: Subject to any disclaimer, the term of this patent is extended or adjusted under 35 U.S.C. 154(b) by 455 days.

(21) Appl. No.: 10/262,503

(22) Filed: Oct. 1, 2002

(65) Prior Publication Data

US 2003/0119090 A1 Jun. 26, 2003

Related U.S. Application Data

(62) Division of application No. 08/122,229, filed on Sep. 15, 1993, now Pat. No. 6,485,930.

(51) Int. Cl.$^7$ .......................... C12N 15/53; C12N 9/10; C12N 15/70
(52) U.S. Cl. ................. 536/23.2; 435/193; 435/252.33; 435/320.1
(58) Field of Search .................. 536/23.2; 435/193, 435/252.33, 320.1

(56) References Cited

U.S. PATENT DOCUMENTS

| | | | |
|---|---|---|---|
| 4,569,909 A | 2/1986 | Seno et al. .................... 435/89 |
| 5,032,519 A | 7/1991 | Paulson et al. ............. 435/193 |
| 5,103,008 A | 4/1992 | Scudder et al. ............... 546/22 |
| 5,180,674 A | 1/1993 | Roth ....................... 435/293.1 |
| 5,246,840 A | 9/1993 | Nilsson ....................... 435/101 |
| 5,264,352 A | 11/1993 | Thiem et al. ................. 435/97 |
| 5,278,299 A | 1/1994 | Wong et al. ................... 536/53 |
| 5,324,663 A | 6/1994 | Lowe ....................... 435/320.1 |
| 6,485,930 B1 * | 11/2002 | Wong ........................... 435/41 |

OTHER PUBLICATIONS

Enzyme Nomenclature (1992) Academic Press, Inc., San Diego pp. 210, 221, 223, 591, 636, 648, 692 and 694.
Lahav et al. (1969) J. Biol. Chem 244, 5890–5898.
Brennan et al. (1968) Biochem. Biophys. Res. Comm.,30, 69–75.
Schutzbach (1980) J. Biol. Chem. 255, 4170–4175.
Jensen et al. (1981) J. Biol. Cehm. 256, 12899–12904.
Sharma et al. (1982) Eur. J. Biochem. 126, 319–325.
Romero et al. (1989) J. Biol. Chem. 264, 1946–1950.
Wang et al., J. Org. Chem., 58:3985–3990 (1993).
Wong et al., Pure & Appl. Chem. 65(4): 803–809 (1993).
Heidlas et al., Acc. Chem. Res., 25:307–314 (1992).
Wong et al., Pure & Appl. Chem., 64:1197–1202 (1992).
David et al., Adv. Carbohydr. Chem. Biochem., 49:175 (1991).
Wong et al., J. Org. Chem., 47:5416 (1982).
Hausler et al., Glycobiology, 2: 77–84 (1992).
Lewis et al., J. Biol. Chem., 266:8255–8251 (1991).
Aoki et al. 1990, The EMBO J. 9(10): 3171–3178.
David, S., et al., Advances in Carbohydrate Chemistry and Biochemistry, vol. 49, "Enzymic methods in preparative carbohydrate chemistry", pp. 175–237. 1991.
Stryer, L., Biochemistry, Third Edition, W.H. Freeman and Co., New York, pp. 343–344, 1988.

* cited by examiner

*Primary Examiner*—Ponnathapura Achutamurthy
*Assistant Examiner*—William W. Moore
(74) *Attorney, Agent, or Firm*—Welsh & Katz, LTD

(57) ABSTRACT

A one-pot glycosylation reaction is disclosed in which a mannosyl (Man) group is enzymatically transferred to an acceptor molecule. The starting glycoside is a mannosyl 1-phosphate that is enzymatically converted to its GDP derivative via UTP and a pyrophorylase. The formed GDP derivative is used in the enzyme-catalyzed glycosyl transfer. That enzyme-catalyzed glycosyl transfer to an acceptor releases GDP that is enzymatically converted to GTP for further conversion of mannosyl 1-phosphate into its GDP derivative. Also disclosed are a recombinant α1,2-mannosyltransferase that is enzymatically active, is dispersible in an aqueous reaction medium, and free of the transmembrane portion of the native enzyme, as well as DNA encoding that transferase, an expression vector containing exogenous DNA that encodes that enzyme and *E. coli* cells containing that vector.

2 Claims, No Drawings

US 6,919,440 B2

MANNOSYL TRANSFER WITH REGENERATION OF GDP-MANNOSE

CROSS-REFERENCE TO RELATED APPLICATION

This is a division of application Ser. No. 08/122,229, filed Sep. 15, 1993 now U.S. Pat. No. 6,485,930, whose disclosures are incorporated herein by reference.

This invention was made with government support under Contract No. GM 44154 awarded by the National Institutes of Health. The government has certain rights in the invention.

TECHNICAL FIELD

The present invention relates to oligosaccharide synthesis, and particularly to the enzyme-catalyzed transfer of a mannosyl group to an acceptor molecule coupled with regeneration of GDP-mannose (GDP-Man).

BACKGROUND ART

The designed enzymatic synthesis of oligosaccharide-containing molecules has recently gained prominence in the art as greater numbers of glycosyltransferase enzymes have become available to skilled workers. See, for instance, U.S. Pat. No. 5,180,674 and allowed U.S. patent application Ser. No. 07/670,701, filed Mar. 18, 1991.

Indeed, U.S. Pat. No. 4,569,909 to Seno et al. teaches the use of uridine diphosphate-N-acetylglucosamine 4-epimerase to epimerize UDP-GlcNAc into an equilibrium mixture of UDP-GlcNAc and UDP-GalNAc. That mixture, after boiling to stop enzymic activity and centrifugation to remove the denatured enzyme, provided a "rough" preparation of UDP-GalNAc that was used with an α-N-acetylgalactosaminyl transferase referred to as "A-transferase" to convert Type O red blood cells into Type A red blood cells.

Seno et al. began each of their reactions with UDP-GlcNAc, a compound that is relatively difficult to prepare and store in large quantity. Seno et al. also had no concept of a regeneration step in which UDP-GalNAc or any other sugar-linked nucleotide is recycled.

Oligosaccharide synthesis based on sugar nucleotide-dependent glycosyltransferases proceeds regio- and stereo-selectively under mild reaction conditions without multiple protection and deprotection step. For review in the field, see Toone, et al., *Tetrahedron*, 45:5365 (1989); David et al., *Adv. Carbohydr. Chem. Biochem.*, 49:175 (1991); Drueckhammer et al., *Synthesis*, 7:499 (1991) and Ichikawa et al., *Anal. Biochem.*, 202:215 (1992). Glycosyltransferases, however, are difficult to obtain (β-1,4-galactosyltransferase is the only one commercially readily available), and the enzymatic synthesis requires sugar nucleotide regeneration for large-scale processes. Wong et al., *J. Org. Chem.*, 47:5416 (1982); Ichikawa et al., *J. Am. Chem. Soc.*, 113:4698 (1991); Ichikawa et al., *J. Am. Chem. Soc.*, 113:6300 (1991); Wong et al., *J. Org. Chem.*, 57:4343 (1992); Ichikawa et al., *J. Am. Chem. Soc.*, 114:9283 (1992).

More than 50 glycosyltransferase genes have been cloned and sequenced from bacteria, yeast and mammalian cells, and documented in the Genebank (IntelliGenetics, Inc.). The availability of these sequences provides researches an opportunity to overexpress glycosyltransferases in large quantities and use them for oligosaccharide synthesis. Of the eight sugar nucleotides commonly used as donor substrates for mammalian glycosyltransferases, five; i.e. UDP-Glc, UDP-Gal, GDP-Fuc, CMP-NeuAc and UDP-Glucuronic acid, have the regeneration system available for large-scale processes. For a review, see Wong et al., *Pure & Appl. Chem.*, 64:1197–1202 (1992).

The enzymes required for the regeneration of GDP-Man, UDP-GlcNAc and UDP-GalNAc have been reported, [Heidlas et al., *Acc. Chem. Res.*, 25:307–314 (1992); Wong et al., *Pure & Appl. Chem.*, 64:1197–1202 (1992)] although regeneration of these sugar nucleotides has not been demonstrated. As part of efforts to develop glycosyltransferase-based enzymatic procedures for the synthesis of complex oligosaccharides and glycopeptides are disclosed hereinafter, as are the overproduction and specificity study of the soluble catalytic domain of an α1,2-mannosyltransferase (ManT), [Lewis et al., *Glycobiology*, 2:77 (1992)]. The application of this enzyme coupled with regeneration of guanosine 5'-diphosphomannose (GDP-Man) to the synthesis of mannose-containing oligosaccharides and glycopeptides are also disclosed hereinafter, and by the present inventor and colleagues in Wong et al., *Pure & Appl. Chem.*, 65(4):803–809 (1993) and Wang et al., *J. Org. Chem.*, 58:3985–3990 (1993).

BRIEF SUMMARY OF THE INVENTION

The present invention contemplates an enzymatic process for transferring a mannosyl group to an acceptor. Transfer of any glycosyl group is referred to as glycosylation, and transfer of a mannosyl group is mannosylation. The contemplated process also recycles the GDP that is formed upon glycosyl transfer to form further amounts of GTP and thereby regenerate the GDP-Man.

In accordance with a contemplated process, an aqueous reaction medium is formed by admixing the following ingredients in an aqueous medium in a single vessel:
(i) a mannosyl (mannose) 1-phosphate (Man-1-P);
(ii) GDP-Man pyrophosphorylase that catalyzes the formation of GDP-Man from Man-1-P in the presence of GTP;
(iii) a mannosyltransferase;
(iv) an acceptor for the mannosyltransferase of (iii); and
(v) a guanosine diphosphate (GDP) recycling system that includes (a) GDP, GTP or both, (b) a phosphate donor, and (c) a kinase to transfer a phosphate group from the phosphate donor to GDP to form GTP. Each of the enzymes of (ii), (iii) and (v) is present in a catalytic amount. The aqueous reaction medium so formed is maintained at a pH value of about 5 to about 10 at a temperature of about zero degrees C. to about 40° C. for a time period sufficient for said acceptor to be glycosylated. The glycosylated acceptor that is formed is preferably recovered.

Also contemplated herein is a recombinant, water-dispersible α1,2-mannosyltransferase, its isolated DNA, an expression vector containing that isolated DNA such as pManflag20, and transformed *E. coli* that contain that vector.

Abbreviations

The various saccharides discussed herein are frequently discussed in their usually used abbreviations. Those abbreviations and saccharide names are listed below as monosaccharides.

GalNAc=N-acetylgalactosamine
Glc=glucose
GlcNAc=N-acetylglucosamine
Man=mannose
Man-1-P=mannose 1-phosphate
Man-6-P=mannose 6-phosphate

DETAILED DESCRIPTION OF THE INVENTION

The present invention contemplates an enzyme-catalyzed glycosyl transfer process in which a mannosyl (Man) group is transferred to an acceptor by an appropriate glycosyltransferase. Mannose is transferred via its 1-GDP derivative as the donor molecule that along with the acceptor is recognized by the glycosyltransferase.

A contemplated process utilizes an aqueous reaction medium containing each enzyme and reactant in a single vessel (one-pot) to carry out the transfer reaction. In accordance with a preferred process, an aqueous reaction medium is formed by admixing the following ingredients in a single vessel along with an aqueous buffer:

(i) Man-1-P;
(ii) GDP-Man pyrophosphorylase that catalyzes the formation of GDP-Man from Man-1-P of (i) in the presence of GTP;
(iii) a mannosyltransferase;
(iv) an acceptor for the mannosyltransferase of (iii); and
(v) a guanosine diphosphate recycling system that includes GDP, GTP or both, a phosphate donor, and a kinase to transfer a phosphate group from the phosphate donor to GDP to form GTP.

Each of the enzymes of (ii), (iii) and (v) is present in a catalytic amount.

The aqueous reaction medium so formed is maintained at a pH value of about 5 to about 10 at a temperature of about zero degrees C. to about 40° C. and for a time sufficient for the acceptor to be glycosylated.

Mannose 1-phosphate (mannopyranosyl 1-phosphate, or mannosyl 1-phosphate or Man-1-P) is a known compound and can be obtained from any one of several literature preparations or from commercial sources such as Sigma Chemical Co., St. Louis, Mo.

It is to be noted that the necessary Man-1-P can be itself formed in situ from Man-6-P via phosphomannomutase, as is known. When Man-1-P is so formed, its concentration is relatively low in solution, at least at the beginning of the reaction, and the total concentration of Man-1-P can be taken as that of both Man-1-P and Man-6-P.

Man-6-P can also itself be formed in situ by the reaction of hexokinase and ATP upon mannose, as is also well known. Thus, when both Man-1-P and Man-6-P are formed in situ, the amount of Man-1-P is deemed to be the total amount of Man plus Man-6-P plus Man-1-P.

Thus, the aqueous reaction mixture can also contain Man, ATP, hexokinase, Man-6-P and phosphomannomutase, as well as the other enzymes and chemical ingredients discussed herein.

A pyrophosphorylase that forms GDP-Man from GTP and mannose 1-phosphate is also present in the aqueous reaction medium. As is disclosed in greater detail hereinafter, freeze dried *Saccharomyces cerevisiae* cells are a convenient source of the required enzyme, GDP-mannose pyrophosphorylase (EC 2.7.7.22).

The before-mentioned Seno et al. U.S. Pat. No. 4,569,909 teaches the addition of sodium pyrophosphate and UDP-GlcNAc pyrophosphorylase to a formed equilibrium mixture of UDP-GlcNAc and UDP-GalNAc to decompose UDP-GlcNAc. That addition was made after the boiling step that deactivates and precipitates the epimerase enzyme, as loss of UDP-GlcNAc while the epimerase is present and active would reverse the equilibrium and remove desired UDP-GalNAc.

In the present process, there is no pyrophosphate added, but is formed in situ and preferably decomposed, and a different pyrophosphorylase is used in recycling the GDP/GTP to make more GDP-Man, rather than decompose the UDP-saccharide or the corresponding GDP-Man.

The mannosyltransferase (Man-T) used is specific for both the transferred mannosyl group and the acceptor to which the Man group is transferred. Mannosyltransferase enzymes that form naturally occurring saccharide linkages are known and have been isolated. A particular mannosyltransferase desired can be prepared as discussed in the literature, and need not be purified as whole cells and cell extracts can be utilized. Several exemplary enzymes are noted hereinafter, with the recombinant α1,2ManT discussed herein being particularly preferred.

The acceptor utilized can be any of a wide variety of oligosaccharides, glycoproteins or glycopeptides. The choice of a particular acceptor is governed to a great extent by the mannosyltransferase employed. In most instances, glycosyltransferase specificity is determined by the non-reducing terminal saccharide alone or in conjunction with about one to about four adjacent saccharides. Thus, once the skilled worker has provided an acceptor having the structural requirements for a given mannosyltransferase to be used, the remaining saccharide or other constituent groups toward either terminus of a saccharide-containing acceptor are not relevant to the transfer reaction, so long as the acceptor possesses minimal solubility in the aqueous reaction medium to be acted upon by the transferase.

Exemplary non-reducing terminal structures formed by reaction of various acceptors with the several mannosyltransferases are noted in *Enzyme Nomenclature*, Academic Press, San Diego, Calif., 1992, and others can be found in the literature such as in Lewis et al., *J. Biol. Chem.*, 266(13):8255–8261 (1991), and are shown below in Table 1 along with common names and EC designations for several of those enzymes:

TABLE 1

GDP-Man Transferases

| Structure | EC Designation | Common Name |
|---|---|---|
| — | 2.4.1.54 | Undecaprenyl-phosphate mannosyltransferase |
| — | 2.4.1.57 | 1-Phosphatidyl-myo-inositol α-mannosyltransferase |
| Manα1→2Manα | 2.4.1.131 | Glycolipid 2-α-mannosyltransferase |
| Manα1→3Manα | 2.4.1.132 | Glycolipid 3-α-mannosyltransferase |
| Manβ1→4GlcNAc-β1→4GlcNAc | 2.4.1.142 | Chitobiosyldiphosphodolichol β-mannosyltransferase |
| Manα1→6Manα | — | Glycolipid 6-α-mannosyltransferase |

The final component in the aqueous reaction medium is a guanosine diphosphate/guanosine triphosphate (GDP/GTP) recycling (regenerating) system. This system recycles GDP that is formed upon glycosyl transfer from GDP-Man to the acceptor, regenerates GTP, and that regeneration is used to form more GDP-Man that can then transferred. The GDP/GTP recycling or regenerating system contains three basic ingredients: (a) GDP, GTP or both, (b) a phosphate donor, and (c) a kinase to transfer a phosphate group from the phosphate donor to GDP.

Either or both of GDP and GTP can be present inasmuch as GDP is converted into GTP, and after the glycosyl transfer reaction, GDP is formed again. Because GDP and GTP interconvert and are reused, the total amount of one or the other is usually discussed rather than amounts for both.

The phosphate donor of the regenerating system is a phosphorylated compound, the phosphate group of which can be used to phosphorylate GDP to form GTP. The only limitation on the selection of a phosphate donor is that neither the phosphorylated nor the dephosphorylated forms of the phosphate donor substantially interferes with any of the reactions involved in the formation of the glycosylated acceptor saccharide. Preferred phosphate donors are phosphoenolpyruvate (PEP) and acetyl phosphate (AcOP). A particularly preferred phosphate donor is PEP, which forms pyruvate (PYR) after phosphate transfer.

The selection of a particular kinase for use in accordance with the present invention depends upon the phosphate donor employed. When acetyl phosphate is used as the phosphate donor, the kinase is acetate kinase (EC 2.7.2.1). When PEP is used as the phosphate donor, the kinase is pyruvate kinase (PK; EC 2.7.1.40). Other kinases can be employed with other phosphate donors as is well known to those of skill in the art. Kinases are commercially available (Sigma Chem. Co., St. Louis, Mo.; Boehringer Mannheim, Indianapolis, Ind.).

Each of the enzymes utilized in the above process is present in a catalytic amount as is discussed further hereinafter.

The enzyme-catalyzed formation of a GDP-Man from a mannose 1-phosphate and GTP also generates inorganic pyrophosphate. In one particularly preferred embodiment, the inorganic pyrophosphate (PPi) formed is enzymatically decomposed to inorganic phosphate (Pi) by inorganic pyrophosphatase (PPase; EC 3.6.1.1) that can also be present in the aqueous reaction mixture in a catalytic amount. The presence of PPi in the aqueous reaction mixture can inhibit some of the enzymes.

A schematic diagram of a general process of the invention is illustrated below in Scheme I, and shows mannosyl transfer to a generalized acceptor R—OH. Three enzymes that can minimally be present are denoted E1–E3, and are identified below the scheme. The production of inorganic pyrophosphate and its consumption by PPase are not shown for greater clarity, although the presence of PPase is preferred, and is shown in Scheme IV, hereinafter.

Scheme I

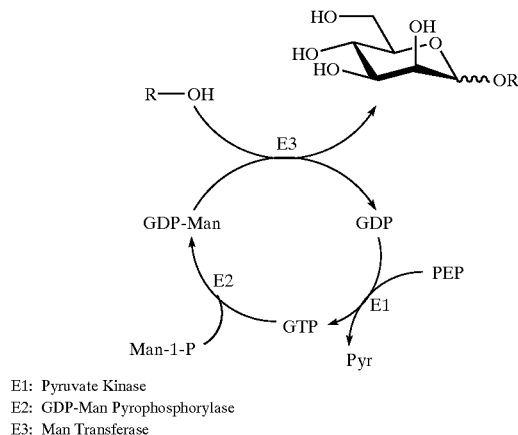

E1: Pyruvate Kinase
E2: GDP-Man Pyrophosphorylase
E3: Man Transferase

As used herein, the phrase "catalytic amount" means that amount of an enzyme at least sufficient to catalyze, in a non-rate limiting manner, the conversion of that enzyme's substrate to product. The catalytic amount of a particular enzyme varies according to the concentration of that enzyme's substrate as well as to reaction conditions such as temperature, time and pH value. Means for determining the catalytic amount for a given enzyme under preselected substrate concentrations and reaction conditions are well known to those of skill in the art.

Admixing comprises mixing each ingredient with each of the other ingredients in a suitable aqueous buffer medium (solvent) to form a reaction mixture or aqueous reaction medium. The aqueous reaction medium is preferably a solution or dispersion of the various components. It is also preferred that the enzymes used be free and not bound to solid supports. Thus, in preferred practice, the aqueous reaction medium is substantially homogeneous.

The temperature utilized can range from about zero degrees C. to the temperature at which the first enzyme denatures, as is readily determined. The process is usually carried out at a temperature of 10° C. to about 40° C. Preferably temperature is from about 15° C. to about 35° C. and, more preferably from about 20° C. to about 30° C. Ambient atmospheric pressure is also preferably utilized.

The pH value can range from about 5.0 to about 10.0. Preferably, the pH value is from about 6.5 to about 8.5 and, more preferably about 7.0 to about 7.5. The pH value is maintained by buffers in the aqueous solvent. The buffer is free of chelators that bind enzyme cofactors such as $Mg^{+2}$ or $Mn^{+2}$ and effectively remove them from the aqueous reaction medium. A chelator such as EDTA can be and preferably is present.

The selection of a buffer is based on the ability of the buffer to maintain pH value at the desired level. Where the pH value is about 7.0–7.5, a useful buffer is HEPES. Where the pH value is about 7.0–9.0, Tris-HCl can also be used.

The osmolality and ionic composition of the aqueous solvent medium are designed and selected to solubilize the ingredients of the reaction mixture in active form, and to provide cofactors for the enzymes contained in the reaction mixture. The osmolality of the aqueous solvent including the buffer is preferably from about 100 mOsm to about 300 mOsm.

Minor amounts (e.g. up to about 25 percent by volume of methanol) of organic solvents that do not substantially inhibit the reaction can also be present to augment solubility of the acceptor. Exemplary solvents include methanol, DMSO, THF, acetone, and acetonitrile. Specific amounts of organic solvents tolerated by recombinant α1,2-Man-T, used as illustrative herein are discussed hereinafter. Solubilizing detergents such as Triton X-100, octyl-beta-D-glucopyranoside (Calbiochem), MEGA-8, -9 or -10 (Calbiochem), CHAPS or CHAPSO (Calbiochem) or Tween-20 that do not denature the enzymes can also be present to improve solubility of the enzymes and acceptor, although it is preferred that the aqueous reaction medium be free of such detergents.

The reaction time and conditions for the glycosylation reaction vary with several parameters such as pH value, the reaction temperature, components of the reactions, their amounts, and the amount of glycosylation desired. Typical reaction times at ambient room temperature (e.g. about 22° C.) range from about one hour where only minimal reaction is desired to about three to about seven days, where substantial consumption of the acceptor and resulting product formation is desired.

The concentration or amount of the various reactants used in a contemplated glycosylation process depend upon numerous factors including reaction conditions such as temperature and pH value, and the amount of acceptor to be glycosylated. Because this glycosylation process utilizes regeneration of GDP in the presence of catalytic amounts of the enzymes, the method is limited by the concentrations or amounts of mannosyl 1-phosphate, phosphate donor and acceptor. The upper limit for the concentrations of reactants that can be used in accordance with the method of the present invention is determined by the solubility of those reactants.

In a preferred embodiment, glycosylation is limited by the concentration of the starting mannosyl 1-phosphate. According to such an embodiment, the concentrations of total GDP, phosphate donor, acceptor and enzymes are selected such that glycosylation proceeds until the starting mannosyl 1-phosphates is substantially consumed.

By way of example, when the concentration of Man-1-P is about 50 mM, preferred concentrations of the other non-enzyme reactants are about 50 mM for the acceptor, about 5 μM for total GDP, and about 50 mM for the phosphate donor. The ratio of the concentration of these reactants to the concentration of monosaccharide phosphate is preferably about 0.9–1.2:1 for the acceptor, about 10–100:1 for GDP and about 1.0–4:1 for the phosphate donor.

The glycosylation (mannosylation) process further preferably comprises isolating or recovering the glycosylated acceptor. Isolation comprises recovering the glycosylated acceptor from the reaction mixture. Means for recovering the glycosylated acceptor include gel filtration, column chromatography, paper chromatography, affinity chromatography, extraction, precipitation and the like, as are well known.

In a preferred embodiment, isolation and recovery are accomplished by lyophilizing the reaction mixture to reduce the volume followed by methanol extraction to remove unreacted acceptor. The lyophilized, extracted reaction mixture is applied to a silica gel column and the glycosylated acceptor compound is eluted from the column with an appropriate solvent as can be readily determined by a skilled worker. The glycosylated acceptor can then be further purified and isolated using usual, well known techniques.

It is to be understood that the glycosylated acceptor need not be isolated (recovered) but can be used in another synthetic step in the aqueous reaction mixture or in another reaction mixture from which the glycosylated acceptor product was not itself previously recovered. For example, where a contemplated process is utilized to form a mannoside to which a GlcNAc group is to be linked to the Man-containing glycoside as with the GlcNAc transferase enzyme GlcNAcT-III (EC 2.4.1.144), it can be advantageous to simply add UDP-GlcNAc and GlcNAcT-III to the reaction mixture to prepare the desired derivative.

In other embodiments, it can be useful to denature and separate the enzymes from the other materials present in the aqueous reaction medium and then add the ingredients required for the next step. This denaturization and separation can be effected by boiling the aqueous reaction medium for a time sufficient to denature the enzymes, e.g. about 5–10 minutes, followed by centrifugation and separation of the resulting precipitate from the supernatant. The supernatant is then used for the next reaction as noted above.

A water-dispersible, enzymatically active glycolipid α1,2-mannosyltransferase (α1,2ManT), its isolated DNA, an inducible expression vector containing that DNA, and transformed E. coli containing that expression vector are also contemplated.

The native yeast (Saccharomyces cerevisiae) α1,2-ManT [Hausler et al., Glycobiology, 2:77–84 (1992)] is a membrane-bound protein that is not readily soluble in an aqueous medium. This native enzyme transfers mannose from GDP-Man to the non-reducing terminal mannose residue of O-linked dimannosyl proteins.

A contemplated recombinant α1,2-ManT is dispersible in an aqueous reaction medium in the absence of a surfactant noted before such as Triton X-100, as has been used for the native enzyme or recombinants containing the native sequence. A contemplated recombinant α1,2-ManT is enzymatically active and transfers a mannose from GDP-Man to a non-reducing terminal mannosyl group.

A contemplated recombinant α1,2-ManT contains the active site of the native enzyme and is substantially free of the membrane-spanning (transmembrane) region. A particularly preferred recombinant enzyme includes the amino acid residue sequence from about position 31 through position 442 of the native enzyme [Lewis et al., J. Biol. Chem., 266:8255–8261 (1991); Hausler et al., Glycobiology, 2:77–84 (1992)].

Isolated DNA that encodes a contemplated enzyme is also contemplated. A preferred, isolated DNA was obtained via PCR using primers Manflag5 (SEQ ID NO:1) and Manflag3 (SEQ ID NO:2) that are discussed in detail hereinafter. Those primers include two different restriction enzyme recognition sequences, Xba I and Sal I, that are in frame with the ompA signal sequence of the vector and α1,2-ManT coding sequence. Primer Manflag3 also includes an in frame stop signal.

The contemplated recombinant α1,2-ManT is preferably expressed in the periplasmic space of E. coli. A such, an expression vector designed for such expression is also preferred. One such IPTG-inducible vector that contains an origin of replication, expression control sequences, a start codon and a periplasmic space signal sequence is available under the designation pFlag from the International Biotech, Inc., New Haven, Conn. The gene encoding a contemplated α1,2-ManT gene is readily inserted into the vector using the PCR-induced restriction sites to form an inducible recombinant DNA vector containing the exogenous α1,2-ManT gene. One such recombinant DNA vector is designated pManflag20.

E. coli transformed with an exogenous α1,2-ManT gene-containing expression vector are also contemplated. Escherichia cell XL1-Blue Strain (Stratagene Co., San Diego, Calif.) so transformed is exemplary of a contemplated transformant. Exemplary E. coli XL1-Blue strain bacteria transformed with pManflag20 were deposited at the American Type Culture Collection (ATCC), 12301 Parklawn Drive, Rockville, Md. 20852 on Mar. 24, 1993 and bear the ATCC accession No. 77379, converted Sep. 14, 1993 to a Budapest Treaty Deposit.

The above deposit was made in compliance with the Budapest Treaty requirements that the duration of the deposit should be for 30 years from the date of deposit or for 5 years after the last request for the deposit at the depository or for the enforceable life of a U.S. patent that matures from this application, whichever is longer. The cells will be replenished should they become non-viable at the depository, and will be made available to the public by the ATCC upon the issuance of a patent from this application.

As is noted hereinafter, expression of enzymatically active α1,2-mannosyltransferase is inducible at an IPTG concentration of less than about 0.01 mM, with a preferred concentration being about 0.005 M IPTG, when the cells are grown in M9-Ca medium.

It was surprising that any enzymatically active protein could be prepared in E. coli as only one other transferase, a soluble galactosyl transferase, has been reported to be expressed from E. coli [Aoki et al., EMBO J., 9(10)

:3171–3178 (1990)], albeit with relatively low biological activity. Other transferases have been expressed in *E. coli*, but those expressed enzymes were not enzymatically active; i.e., the α1,2ManT expressed here transfers Man from GDP-Man to an acceptor (is enzymatically active), whereas with the one exception above, glycosyltransferases expressed in *E. coli* did not transfer their glycosyl group (enzymatically inactive).

Results

The α1,2-mannosyltransferase (α1,2-ManT) in the yeast *Saccharomyces cerevisiae* is a membrane-bound enzyme that transfers mannose GDP-mannose to the terminal mannose residue of O-linked dimannosyl proteins [Lewis et al., *Glycobiology*, 2:77 (1992)]. Similar to known glycosyltransferases and glycosidases of the mammalian Golgi apparatus [Joziasse, *Glycobiology*, 2:271 (1992)], this ManT contains a short N-terminal domain followed by a membrane-spanning region and a large catalytic domain.

As it has been shown that the catalytic domains of many glycosyltransferases are more stable and as active as the membrane-bound enzymes, [Paulson et al., *J. Biol. Chem.*, 264:17615 (1989)] a secretion vector harboring the gene encoding the catalytic domain of the mannosyltransferase for overexpression in *E. coli* has been constructed. Most of glycosyltransferases were expressed in CHO cells [Joziasse, *Glycobiology*, 2:271 (1992)]. The only example for the expression of the catalytic domain of glycosyltransferase in *E. coli* is that of β-galactosyltransferase that had a low enzymatic activity. Aoki et al., *EMBO J.*, 9:3171 (1990). Other attempts to express other enzymatically active glycosyltransferases in *E. coli* have not been successful. It was found that some O-linked mono-mannosyl peptides are better substrates than mannose and mannobiose for the recombinant enzyme.

Overexpression and Purification of the Mannosyltransferase

The gene encoding the protein sequence 31–442 of α1,2-ManT from *S. cerevisiae* was cloned by the PCR method with two digested primers as described in Wang et al., *J. Org. Chem*, 58:3985–3990 (1993). The 5' primer, Manflag5, from its 5' terminus, contained the bases ATATT linked to an Xba I recognition sequence that itself was linked to 18 bases corresponding to the sequence of the protein beginning at N-terminal amino acid residue position 31. The 3' primer, Manflag3, from its 5' terminus contained the sequence GCGC linked to a Sal I recognition site that was linked to two stop codons (TTATTA) that were linked to 18 bases that coded for C-terminal amino acid residue position 442 and then upstream on the protein. Those two primers are shown below.

Manflag 5:
(SEQ ID NO:1)
5' ATATTTCTAGAAGAACTCAGCAATATATT

Manflag 3:
(SEQ ID NO:2)
5' GCGCGTCGACTTATTACTCACGGAATTTTTTCCA

The PCR insert (1.4 kb) corresponding to the α1,2-ManT gene was digested with Xba I and Sal I, and was ligated into vector pFlag (purchased from International Biotech, Inc., New Haven, Conn.) to construct the plasmid pManflag20. That plasmid was then transformed into *E. coli* XL1-Blue strain [Maniatis et al., *A Laboratory Manual*, Cold Spring Harbor, N.Y. (1989); Rose et al., *Methods in Yeast Genetics: A Laboratory Course*, Cold Spring Harbor Lab., New York (1990)] for overproduction of the enzyme.

The activity of α1,2-ManT expressed in *E. coli* was found dependent on the culture condition. When the cells were cultured in the LB medium or M9 medium at 37° C. with the inducer (isopropyl-β-D-thiogalactopyranoside, IPTG) concentration at 1 mM (standard conditions), no mannosyltransferase activity could be detected in the culture. In contrast, when the cells were grown at 30° C. in M9-Ca medium [Takagi et al., *Biotechnology*, 6:948 (1988)] in the presence of a very low concentration of IPTG (<0.01 mM), significant amounts of α1,2-ManT activities were obtained.

This latter result indicated that at these conditions the recombinant protein was properly folded and secreted into the *E. coli* periplasmic space [Shibui et al., *Appl. Microbiol. Biotechnol.*, 37:352 (1992); Hsuing et al., *Biotechnology*, 4:991 (1986)]. The optimal concentration of IPTG was found to be around 0.005 mM. At this concentration, one liter of culture yields 0.7–0.8 units [one unit transfers 1.0 μmol of mannose from GDP-mannose to a methyl α-D-mannopyranoside per minute at 30° C.] of α1,2-ManT.

Because most of the active enzyme is secreted in the periplasmic space, purification of the recombinant protein is very straightforward. After the perplasmic fraction is prepared from the cells as described hereinafter, the fraction can be directly used for the synthetic purpose, although minor phosphatase activities were also found in this fraction. To prevent the decomposition of sugar nucleotide during the enzymatic mannosylation reaction, an inhibition cocktail (about 1 percent volume) containing 100 mM ATP (serves as a "scape-goat"), 1 mM theophylline [Metaye et al., *Biochem. Pharmacol.*, 37:4263 (1988)] and 1 mM 2,3-dimercaptopropanol [Cottrell et al., *Biochem J.*, 283:299 (1992)] was added.

After a Superose column chromatography, further purification of ManT was carried out by FPLC on a Mono Q column to obtain the protein with a specific activity of about 1 unit/mg. The purity of the protein was assessed by SDS-polyacrylamide gel electrophoresis and was estimated to be greater than 85 percent with a molecular weight of 50 kDa.

Enzyme Stability

The recombinant enzyme retained more than 90 percent activity after four days in a buffer at 20° C. solution (100 mM Tris-HCl, 5 mM $MgCl_2$ buffer, pH 7.4). However, at a higher temperature (37° C.) the enzyme showed a half-life of about four hours. The oligosaccharide synthesis was conducted at 25–30° C.

Organic Solvent Effects

Because a low concentration of organic solvent is needed to dissolve some of O-glycopeptides used as acceptors in this work, the effect of organic solvent on the mannosyl-transfer reaction was investigated. The enzyme tolerates up to 30 percent of methanol and 20 percent acetone-buffer solution. The transferase remains about 80 percent active in a 10 percent DMF-buffer solution and about 50 percent active in a 10 percent acetonitrile-buffer solution, but loses 95 percent of activity when the concentrations of these organic solvents increase to 20 percent. Thus, when needed in the assay and synthesis, 10 percent acetone or up to 25 percent methanol-buffer solution is utilized.

Substrate Specificity

Previous studies on the native α1,2-mannosyltransferase showed that the enzyme transferred mannose to α-methyl mannopyranoside and mannobiose. [Lehle et al., *Biochem. Biophys. Aca.*, 350:225 (1974); Jung et al., *Eur. J. Biochem.*, 37:1 (1973); Babczinski et al., *Biochem. Biophys. Res. Commun.*, 54:1119 (1973)]. The active domain of the recombinant prepared in this study also has a similar substrate specificity (Table 2, below).

Thus, this recombinant enzyme accepts α-methylmannopyranoside (Compound 1), mannose (Compound 2) and Manα1→2ManαOMe (Compound 3) as substrates with $K_m$ values of 57, 193 and 28 mM, respectively. For comparison, the $K_m$ value of mannose for the native enzyme was 100 mM [Lehle et al., *Biochem. Biophys. Aca.*, 350:225 (1974); Jung et al., *Eur. J. Biochem.*, 37:1 (1973); Babczinski et al., *Biochem. Biophys. Res. Commun.*, 54:1119 (1973)]. The C-6 modified α-methyl-mannopyranosides such as 6-deoxy-ManαOMe (Compound 4), 6-azido-6-deoxy-ManαOMe (Compound 5) and 6-amino-6-deoxy-ManαOMe (Compound 6) are poor substrates. p-Nitrophenyl α-mannopyranoside and other monosaccharides with an S-configuration at 2 position such as D-altrose, D-idose, D-talose, D-arabinose and D-lyxose are not substrates. The mannosidase inhibitor, 1-deoxymannojirimycin, (synthesized via fructose diphosphate aldolase catalyzed condensation followed by catalytic intramolecular reductive amination [Kajimoto et al., *J. Am. Chem. Soc.*, 113:6187 (1991)] was neither a substrate nor an inhibitor of α1,2-ManT.

TABLE 2

Relative Rates and $K_m$ (acceptor) of the mannosyltransfer reaction (GDP − Man + acceptor) Catalyzed by the Recombinant α1,2-Mannosyltransferase

| Compound | | $V_{relative}$[a] | $K_m$(mM0) |
|---|---|---|---|
| ManαOMe | (1) | 1.0 | 57 |
| Mannose | (2) | 0.46 | 193 |
| Manα1,2ManαOMe | (3) | 0.62 | 28 |
| 6-Deoxy-ManαOMe | (4) | 0.06 | |
| 6-Azido-6-deoxy-ManαOMe | (5) | 0.02 | |
| 6-Amino-6-deoxy-ManαOMe | (6) | 0.07 | |
| Cbz-Thr-Val-OMe<br>\|α<br>Man | (7) | 0.71 | 7.8 |
| H-Thr-Val-OMe<br>\|α<br>Man | (8) | 0.68 | |
| Cbz-Thr-Val-Gly-Ala-NH$_2$<br>\|α<br>Man | (9) | 0.55 | |
| Boc-Tyr-Thr-Val-OMe<br>\|α<br>Man | (10) | 0.35 | 0.7 |
| Cbz-Thr-Val-OMe<br>\|α<br>Man<br>\|α1,2<br>Man | (11) | 0.17 | 26 |

TABLE 2-continued

Relative Rates and $K_m$ (acceptor) of the mannosyltransfer reaction (GDP − Man + acceptor) Catalyzed by the Recombinant α1,2-Mannosyltransferase

| Compound | | $V_{relative}$[a] | $K_m$(mM0) |
|---|---|---|---|
| 6-O-Tosyl-ManαOMe | (12)[b] | 0.00 | |
| p-nitrophenyl α-mannopyranoside | (13)[b] | 0.00 | |

[a]Calculated as the ratio of $V_{max}$.
[b]Other unacceptable substrates assayed are discussed in the text below.

O-mannosylpeptides were found to be good substrates for this enzyme. For example, Cbz-Thr(α-Man)-Val-OMe (Compound 7) is comparable with ManαOMe as an acceptor, but has lower $K_m$ value. The N-terminal deprotected Compound 8 and longer peptide analog Compound 9 are also good substrates. Interestingly, O-glycopeptide Compound 10 with the peptide sequence Tyr-Thr-Val [Tanner, *Eur. J. Biochem.*, 196:185 (1991)] has an $K_m$ value of 0.7 mM for α1,2-ManT. This value is 10 times less than that of Compound 7 and 80 times smaller than that of ManαOMe (Compound 1). This result suggests that α1,2-ManT prefers certain peptide sequences in O-mannosylpeptides.

Oligomannose is the backbone structure component of N-linked and O-linked glycoproteins in yeast and mammalian cells. Such oligosaccharides are constructed by the highly ordered addition of monosaccharide units to the growing oligosaccharide chain.

Recent studies on the biosynthesis of O-linked carbohydrate chains in *S. cerevisiae* suggested that the native α1,2-mannosyltransferase was responsible for the transferring of the third mannose to the growing O-linked carbohydrate chains [Hausler et al., *Proc. Natl. Acad. Sci.*, 89:6846 (1992)]. However, comparing kinetic data for Compounds 7 and 11, the recombinant active domain of α1,2-ManT seems more active on monomannosyl O-glycopeptides than on dimannosyl glycopeptides. The reason for this observation is not clear yet.

The C-6 modified α-methyl-mannopyranosides used in the specificity study were synthesized from Compound 1 (Scheme II, below). Thus, tosylation of Compound 1 in pyridine at zero degrees C., followed by substitution and reduction, provided Compounds 12, 5 and 6, respectively. Bromination of the 6-hydroxyl group of Compound 1 and subsequent acetylation afforded Compound 14. Reduction of Compound 14 with Bu$_3$SnH, followed by deprotection, gave 6-deoxy derivative, Compound 4.

Scheme II

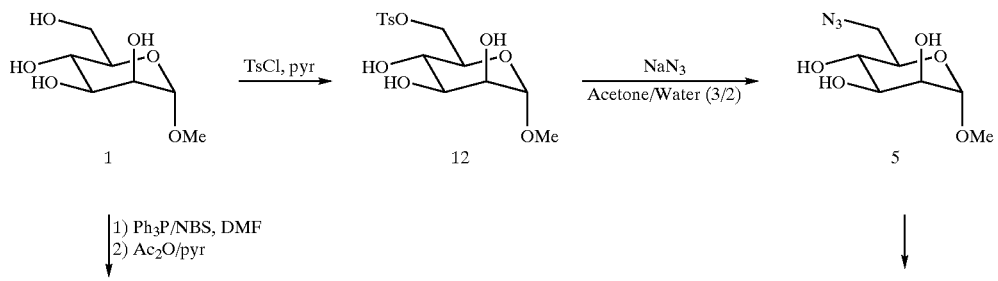

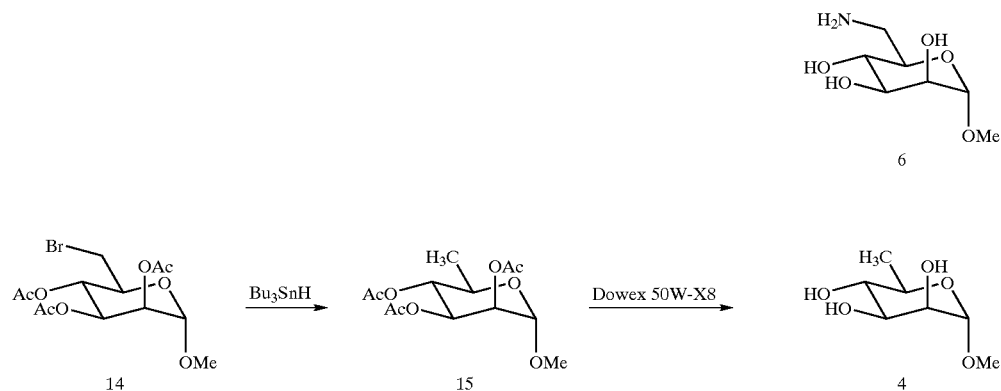

The O-mannosylpeptides in Table 2 were prepared chemically and the peptide chain was extended either chemically or enzymatically as shown in Scheme III, below. The O-glycopeptide Compound 16 was synthesized by glycosylation of peptide Cbz-Thr-Val-OMe with tetraacetyl-O-D-mannopyranosyl bromide in the presence of silver trifluoromethanesulfonate [Garegg, et al., *Acta Chem. Scand.*, B33 (1979); Schultheiss-Reimann et al., *Angew. Chem. Int. Ed. Enl.*, 22:62 (1983); Hanessian et al., *Carbohydrate Res.*, 53:C13 (1977)]. Compound 10 was synthesized from Compound 17 by a standard peptide coupling reaction from Boc-Tyr(Bzl)-OH. Deacylation of Compound 16 in NaOMe/MeOH at zero degrees C. afforded Compound 7. Compound 9 was synthesized via coupling of Compound 7 with H-Gly-Ala-NH$_2$ catalyzed by a subtilisin mutant 8397 [Zhong et al., *J. Am. Chem. Soc.*, 113:683 (1991)] in 80 percent DMF (v/v) solution. This protease was developed for use in DMF and has proven to be an effective catalyst for the synthesis of O- and N-glycopeptides.

Scheme III

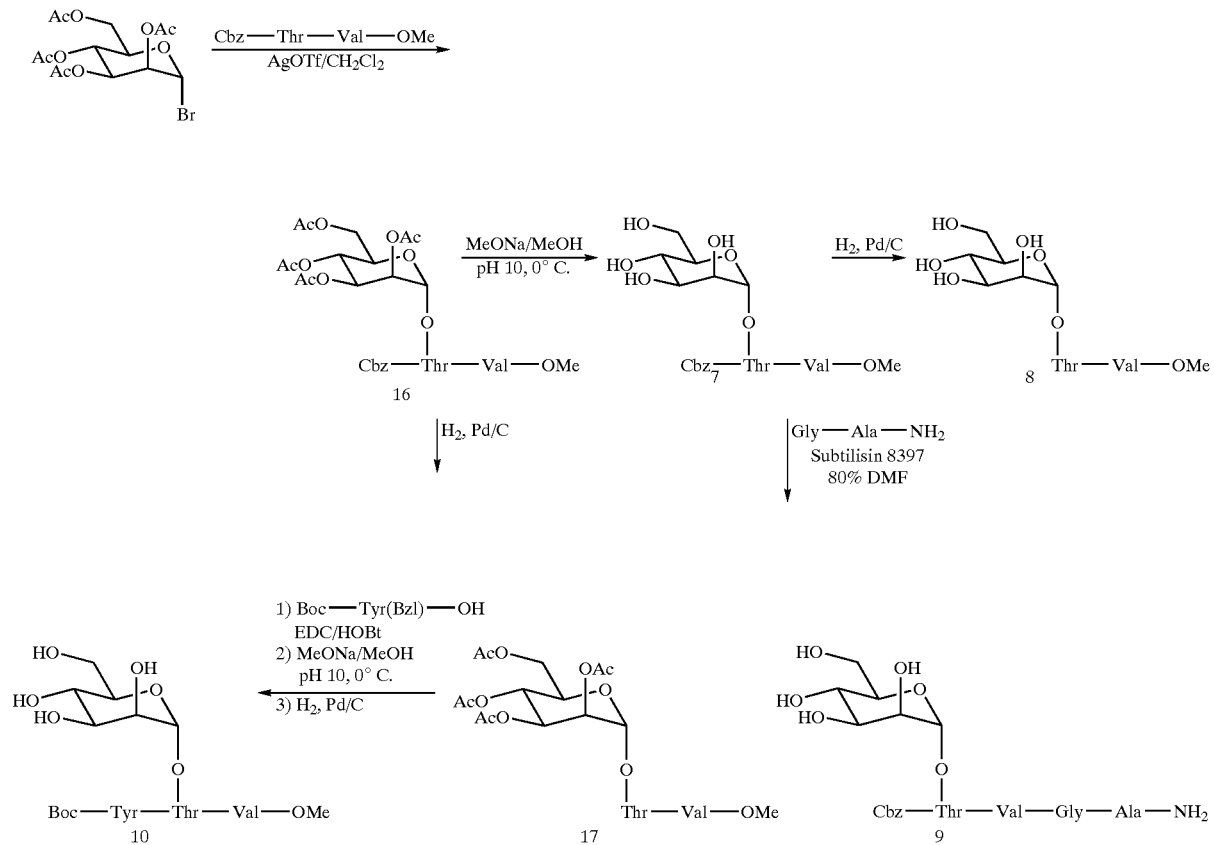

Synthesis of Mannose-containing Saccharides and Glycopeptides with Regeneration of GDP-Man A particularly preferred mannosyltransferase-catalyzed cyclic mannosylation process is illustrated in Scheme IV, below. The products of this glycosylation process, Compound 3 and 11, are shown below the scheme. The numbered enzymes are identified below the scheme.

Scheme IV

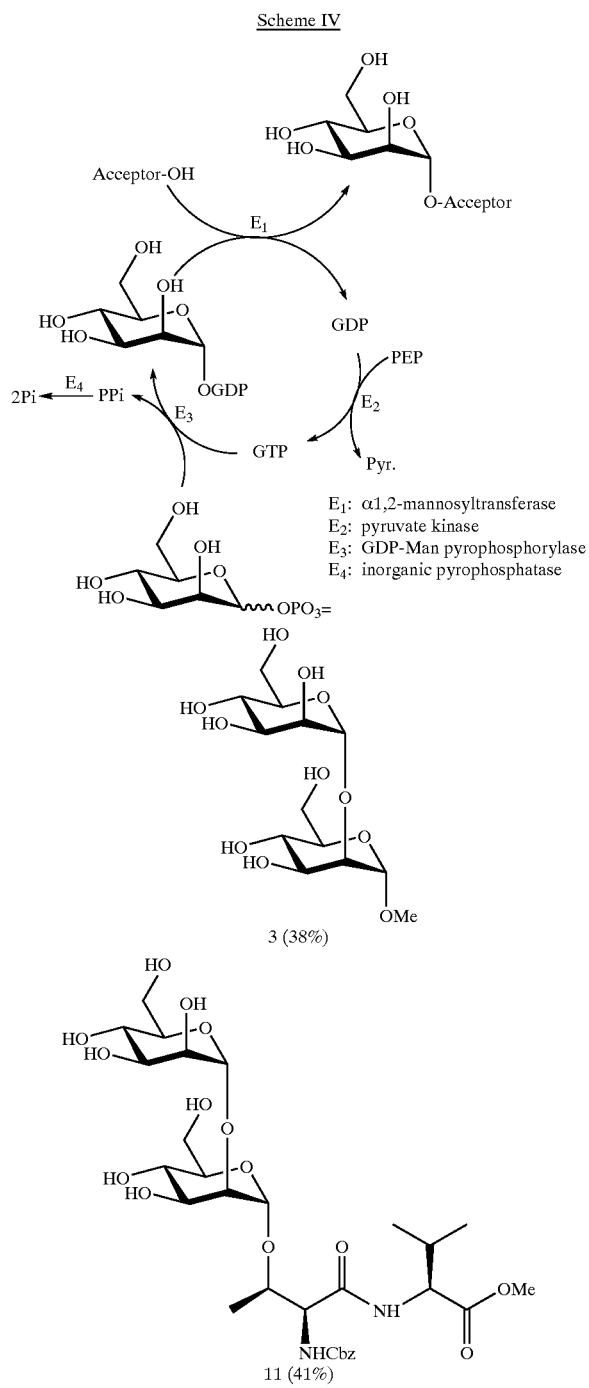

Thus, the multi-enzyme system started with mannose 1-phosphate (Man-1-P) which was synthesized from mannose in three steps in this laboratory [Sim et al., *J. Am. Chem. Soc.*, in press]. Mannose 1-phosphate reacted with GTP catalyzed by GDP-mannose pyrophosphorylase (EC. 2.7.7.22) from yeast cells. GDP-mannose pyrophosphorylase was more stable in lyophilized cells than in a cell-free extract. No degradation of generated GDP-mannose was observed when EDTA (5 mM) was added to the reaction solution [Simon et al., *J. Org. Chem.*, 55:1834 (1990)] to form GDP-Man. [Cabib et al., *J. Biol. Chem.*, 206:779 (1954); Wood, *J. Biol. Chem.*, 239:3119 (1964)]. GDP-Man was consumed by ManT to give the mannose-containing oligosaccharide or glycopeptide (shown generically in Scheme IV as Acceptor-OH), and the released GDP was again converted to GTP by pyruvate kinase (PK EC 2.7.7.9) and phospho(enol)pyruvate (PEP). The pyrophosphate (PPi) resulting from the reaction was hydrolyzed to phosphate (Pi) by inorganic pyrophosphatase (EC 3.6.1.1) to shift the equilibrium and to avoid its inhibition.

It is noted that glycolipid 3-α-mannosyltransferase could have been used here to form Manα1→3Man-OMe, instead of Compound 3. Similarly, either the 6-α- or 6-β-mannosyltransferase could be used to form the corresponding Manα1→6Man-OMe or Manβ1→6Man-OMe. Of course, the isolated native α1,2-Man-T (EC 2.4.1.131) could also have been used.

In a representative synthesis of Cbz-Thr(α-Man1, 2αMan)-Val-OMe (Compound 11), a reaction mixture (2 mL, 100 mM Tris, pH 7.5, 5 percent acetone, 10 mM MgCl$_2$, 10 mM MnCl$_2$, 5 mM EDTA, 5 mM NaN$_3$, 1 mM ATP, 0.01 mM theophylline, 0.03 mM 2,3-dimercaptopropanol and 0.05 mM phenylmethylsulfonyl fluoride) containing Cbz-Thr(α-Man)-Val-OMe (acceptor, Compound 7; 100 mg, 95 mM), mannose 1-phosphate (60 mg, 100 mM), GDP (9 mg, 10 mM), PEP (47 mg, 100 mM), pyruvate kinase PK (50 U), dried yeast cells (50 mg), α1,2-ManT (0.4 U) and inorganic pyrophosphatase (1 U) was slightly stirred at room temperature for 60 hours, then centrifuged. The supernatant was lyophilized and extracted with methanol. After removal of the methanol, the product was purified by silica gel column chromatography (CHCl$_3$:CH$_3$OH:H$_2$O=6:3:0.5, v/v/v) to afford Cbz-Thr(α-Man1→2αMan)-Val-OMe, (Compound 11; 31 mg) in 41 percent overall yield based on consumed Cbz-Thr(α-Man)-Val-OMe. The disaccharide Compound 3 was prepared in a similar manner in 39 percent yield.

Experimental Section General

All chemicals were purchased from commercial sources as reagent grade. Fast protein liquid chromatography (FPLC) was performed on a Pharmacia system composed of two P-500 pumps, a GP-250 gradient programmer, and a single-path UV-1 monitor. UV-visible spectrum was recorded on a Beckman DU-70 spectrometer. SDS-PAGE was carried out on Pharmacia Phast System. $^1$H and $^{13}$C NMR spectra were recorded on Bruker AMX-500 spectrometer. High resolution mass spectra (HRMS) were recorded on a VG ZAB-ZSE mass spectrometer under Fast Atom Bombardment (FAB) conditions. Thin-layer chromatography was conducted on Baker Si250F silica gel TLC plates with fluorescent indicator. Column chromatography was conducted with silica gel, grade 62, 60–200 mesh, and 150 Å. Enzymes such as pyruvate kinase and inorganic pyrophosphatase were purchased from Sigma Co. The vector pFlag-1 was purchased from International Biotech. Inc. (New Haven, Conn.).

Amplification of the α-1,2-Mannosyltransferase Gene from Yeast DNA

A PCR amplification was performed in a 100 mL reaction mixture containing 1 μL (0.5 μg) of yeast (*Saccharomyces cerevisiae*) DNA, [Maniatis et al., *Molecular Cloning: A Laboratory Manual*, Cold Spring Harbor, N.Y. (1989); Rose et al., *Methods in Yeast Genetics: A Laboratory Course*, Cold Spring Harbor Lab., New York (1990)], 400 nmol of the primers Manflag5 and Manflag3, 200 mM of different dNTPs, 50 mM KCl, 10 mM Tris-HCl (pH 8.3), 2 mM $MgCl_2$, 0.01 percent Triton X-100, and two units of *Thermus aquaticus* DNA polymerase, as noted in Wang et al., *J. Org. Chem.*, 58:3985–3990 (1993). The reaction was overlaid with 100 μL mineral oil and subjected to 30 cycles of amplifications.

Construction of the α1,2-Mannosyltransferase Expression Vector

The DNA obtained from the PCR amplification was extracted with phenol/chloroform and precipitated with ethanol at −70° C. for 30 minutes. The precipitated DNA was centrifuged and washed with 70 percent ethanol. The DNA pellet (about 500 μg) was then dissolved in a restriction enzyme buffer and digested with Xba I and Sal I (40 U each) at 37° C. for two hours. The digested DNA was then recovered by phenol/chloroform extraction and ethanol precipitation. The DNA was redissolved in 50 μL of TE buffer (pH 7.7) and purified on 0.7 percent agarose gel. The DNA band corresponding to 1.4 kb was separated from the agarose gel and purified with Gene Clean kit (Bio-101 Co., San Diego). and was used as an insert.

The vector prepared from digestion of pFlag-1 DNA (1 mg) with 40 units of Xba I and Sal I was recovered with ethanol precipitation after extraction with phenol/chloroform, and further purified by agarose gel as described in the insert preparation. The insert was then ligated to the vector and transformed to *E. coli* XL1-Blue strain and plated on LB agar plates which contained 100 mg/mL ampicillin.

Screening for Positive Clones

Because the host strain *E. coli* does not contain yeast α1,2-mannosyltransferase gene, only the positive clones that contain this gene show the PCR amplification product of 1.4 kb when primers Manflag5 and Manflag3 are used. Therefore, the PCR method was used for the screening.

Thirty-three colonies were randomly selected from plates and lysed with 50 μL of a cell lysing buffer (20 mM Tris-HCl containing 1 percent Triton X-100 and 2 mM EDTA, pH 8.5). Heated with boiling water for 5 minutes, the solution was used as a DNA template source for PCR amplification. The procedure for the PCR amplification was the same as that described in the amplification of α1,2-mannosyltransferase gene except 3 μL of the cell lysing solution was used to replace yeast DNA. Three positive clones were identified. The resulting α1,2-mannosyltransferase expression vector was called pManflag20.

Growing Transformed *E. coli* Strain

The transformed *E. coli* strain was grown on M9-CA medium ($Na_2O_4 \cdot 7H_2O$, 12.8 g; $KH_2PO_4$, 3.0 g; NaCl, 0.5 g; $NH_4Cl$, 1.0 g; technical grade casamino acids, 20.0 g; water, 1 liter) containing 1 mM $CaCl_2$ and 100 μg/mL ampicillin to mid-logarithmic phase ($OD_{600}$ 0.5–0.6) at 37° C. and then induced with 0.005 mM IPTG for 12 hours at 30° C. with shaking.

Preparation of α1,2-ManT from *E. coli* Periplasmic Space

This preparation was carried out following well known literature procedures. [See, Lehle et al., *Biochem. Biophys. Acta.*, 350:225 (1974); Jung et al., *Eur. J. Biochem.*, 37:1 (1973); Babczinski et al., *Biochem. Biophys. Res. Commun.*, 54:1119 (1973).]

Briefly, all steps were carried out at 4° C. The culture from 5 liters of grown *E. coli* cells was centrifuged at 10,000×g for 10 minutes. The cell pellet was resuspended in 200 mL of 20 percent sucrose, 10 mM Tris-HCl (pH 7.6). To the suspension were added 4 mL of EDTA (0.5 M), and the sample was incubated on ice for 30 minutes, then centrifuged for 5 minutes at 4° C. After removal of the supernatant, the pellet was resuspended in 20 mL cold distilled water. The suspension was incubated for 30 minutes on ice, and then centrifuged for 5 minutes. The supernatant (the periplasmic fraction) was carefully removed; then 1 mL of 2 M Tris-HCl, 100 mM $CaCl_2$ solution was slowly added to the supernatant. After incubation on ice for 10 minutes, the suspension was centrifuged for 5 minutes and the precipitates were discharged. The supernatant was then dialyzed against 100 mM Tris-HCl (pH 7.6) for 8 hours at zero degrees C. Activity assay showed the resulting periplasmic fraction (20 mL) has approximately 3.7 units of ManT activity.

α1,2-Mannosyltransferase Activity Assay

GDP-Man ($^{14}$C) (10 mM, 10 mL), α-methyl mannopyranoside (500 mM, 10 μL) and the enzyme solution (10 μL) were mixed in a buffer containing 50 mM HEPES (pH 7.2), 0.1 percent Triton and 10 mM $MnCl_2$. The mixture was incubated at 30.0° C. for one hour. The unreacted GDP-mannose was removed by adding QAE-Sephadex (400 μL) to the solution. After the resin was removed by centrifugation, the radioactivity of the solution was counted in 10 mL of scintillation fluid. Controls were carried out by omitting the acceptor or the enzyme.

Enzyme Stability Study

The enzyme was incubated at room temperature in 100 mM Tris-HCl buffer, 5 mM $MgCl_2$, pH 7.4, containing 0.5 mM dithiothreitol. At different time intervals, 10 μL aliquots were taken and assayed for mannosyltransferase activity as described above.

Organic Solvent Effect Study

GDP-Man ($^{14}$C) (10 mM, 10 μL) and methyl mannopyranoside (500 mM, 10 μL) were mixed with a certain volume of an organic solvent and $H_2O$ to achieve the desired organic solvent concentration. The enzyme (10 μL) was then added to the mixture. The solution was incubated at 30.0° C. for 1 hour. The enzyme activity was measured as described in the enzyme assay section.

Substrate Specificity and Enzyme Kinetics

The substrate specificity was determined in a 30 μL assay solution containing 150 mM substrate, 3.3 mM GDP-Man, overproduced α1,2-ManT, 50 mM HEPES (pH 7.2), 0.1 percent Triton and 10 mM $MnCl_2$. The mixture was incubated at 30° C. for 1 hour and the formation of product was determined by the radioactivity assay. Initial velocities were measured as described in the enzyme assay at various concentrations of acceptors for kinetic studies. From the Lineweaver-Burk plots of the data, $K_m$ and $V_{max}$ were determined.

GDP-Mannose Pyrophosphorylase

Yeast (*Saccharomyces cerevisiae*) was grown in YM broth (Yeast extract, 3 g, Malt extract, 3 g; Bacto peptone, 5 g; Bacto dextrose, 10 g per liter distilled water, pH 6.2) with supplement of 1 percent sucrose. The culture was grown at 30° C. with shaking (250 rpm) for 36 hours and then centrifuged at 8,000×g (4° C.) for 20 minutes to recover the cells. The cells were washed once with Tris-HCl buffer (100 mM, pH 7.5 with 5 mM $MgCl_2$ and 1 mM mercaptoethanol) and then lyophilized and used as the GDP-mannose pyrophosphorylase source.

Compound Synthesis

Methyl 2,3,4-tri-O-acetyl-6-bromo-6-deoxy-α-D-mannopyranoside (Compound 14)

Triphenylphosphine (5.4 g, 20.6 mmol) was added portionwise to a cooled solution of methyl α-D-mannopyranoside (2.0 g, 10.3 mmol) and NBS (3.66 g, 20.6 mmol) in DMF (100 mL) at 0–5° C., and the mixture was heated at 50° C. for 2 hours. After cooling, MeOH (5 mL) was added dropwise and the mixture was concentrated. The residue was acetylated with Ac$_2$O (20 mL) and pyridine (30 mL). The product was purified by silica gel column chromatography, with toluene-EtOAc (10:1) to give Compound 14 (1.74 g, 44 percent). $^1$H NMR (500 MHz, CDCl$_3$) δ 2.00, 2.07, 2.15 (s, 3H, 3×OAc), 3.41–3.49 (m, 2H, H-6), 3.46 (s, 3H, OMe), 3.98 (ddd, 1H, J=3.0, 8.0, 9.5 Hz, H-5), 4.74 (d, 1H, J=1.65 Hz, H-1), 5.19 (t, 1H, J=9.92 Hz, H-4), 5.23 (dd, 1H, J=1.70, 3.42 Hz, H-2), 5.33 (dd, 1H, J=3.42, 9.97 Hz, H-3). $^{13}$C {1H} NMR (CDCl$_3$) δ 20.60, 20.69, 20.79, 31.32, 55.31, 68.64, 68.77, 69.41, 69.89, 98.35, 169.77, 169.96. HRMS calculated for C$_{13}$H$_{19}$O$_8$BrCs$^+$ (M+Na$^+$) 514.9318, found 514.9318.

Methyl 6-Deoxy-α-D-mannopyranoside (Compound 4)

A solution of Bu$_3$SnH (1.97 g, 6.77 mmol; 1.82 mL) in toluene (40 mL) was added dropwise to a gently refluxing solution of 14 (1.70 g, 4.42 mmol) in toluene (40 mL) over 20 minutes, and the mixture was refluxed for 10 hours. After cooling, the mixture was concentrated, and the residue was chromatographed on silica gel, with toluene-EtOAc (30:1) to give methyl 2,3,4-tri-O-acetyl-6-deoxy-α-D-mannopyranoside. A solution of this compound (700 mg, 2.30 mmol) and methanolic MeONa (1 mL, 0.3 M solution) in MeOH (30 mL) was stirred for 2 hours at room temperature. The mixture was neutralized by addition of Dowex 50W-X8, then the resin was filtered off, and the filtrate was concentrated to give Compound 4 (327 mg, 80 percent yield). $^1$H NMR (500 MHz, CD$_3$OD) δ 1.26 (d, 3H, J=6.5 Hz, H-6), 3.33 (s, 3H, OMe), 3.37 (m, 1H), 3.51–3.55 (m, 1H), 3.59 (dd, 1H, J=3.5, 9.5 Hz), 3.76 (dd, 1H, J=2.0, 3.5 Hz), 4.54 (d, 1H, J=1.5 Hz, H-1). $^{13}$C {1H} NMR (CD$_3$OD) δ 18.01, 55.12, 69.67, 72.25, 72.44, 73.90, 102.83. HRMS calculated for C$_7$H$_{14}$O$_5$Na$^+$ (M+Na$^+$) 201.0739, found 201.0745.

6-Tosyl-ManαOMe (Compound 12)

α-Methyl mannopyranoside (1.5 g, 7.8 mmol) was dissolved in 20 mL dry pyridine and cooled to zero degrees C. Then tosyl chloride (2.0 g, 10.3 mmol) was slowly added. The reaction was kept stirring at zero degrees C. for 8 hours. The solvent was removed in vacuo and the residue was chromatographed on silica gel, eluting with hexane/EtOAc=1/4, to afford Compound 12 (2.02 g, 74 percent yield). $^1$H NMR (500 MHz, CDCl$_3$) δ 2.42 (s (3H), 3.28 (s, 3H), 3.70–3.75 (m, 3H), 4.25–4.34 (m, 3H), 4.65 (s, 1H), 7.26–7.33 (m, 2H), 7.78–7.80 (m, 2H). $^{13}$C {1H} NMR (CDCl$_3$) δ 21.00, 55.01, 66.95, 69.58, 69.97, 70.45, 71.58, 128.01, 129.83, 129.98, 132.60, 145.00.

6-Azido-6-deoxy-ManαOMe (Compound 5)

6-Tosyl-ManαOMe Compound 12 (100 mg, 0.28 mmol) was dissolved in 10 mL solvents (acetone/H$_2$O=3/2). Sodium azide (56 mg, 0.86 mmol) was added. The reaction was refluxed under N$_2$ for 12 hours. Then the solvents were removed in vacuo, the residue was extracted with 50 mL of methanol and chromatographed with silica gel, eluting with CHCl$_3$/MeOH/H$_2$O=6/3/0.5, to give the desired product, Compound 5 (55 mg, 86 percent yield). $^1$H NMR (500 MHz, CD$_3$OD) δ 3.30 (s, 3H), 3.32 (m, 2H), 3.46–3.54 (m, 3H), 3.70 (dd, 1H, J=2.0, 3.5 Hz), 4.54 (d, 1H, J=2.0 Hz). $^{13}$C {1H} NMR (CD$_3$OD) δ 52.92, 55.30, 69.45, 71.90, 72.33, 73.78, 102.80. HRMS calculated for C$_7$H$_{13}$N$_3$O$_5$Na$^+$ (M+Na$^+$) 242.0753, found 242.0761.

6-Amino-6-deoxy-ManαOMe (Compound 6)

Hydrogenolysis of Compound 5 (24 mg) in 2 mL methanol in presence of Pd/C produced Compound 6 (18 mg, 85 percent yield). $^1$H NMR (500 MHz, D$_2$O) δ 2.7 (dd, 1H, J=7.0, 13.5 Hz), 2.90 (dd, 1H, J=3.0, 13.5 Hz), 3.28 (s, 3H), 3.32–3.33 (m, 1H), 3.35 (t, 1H, J=2.5 Hz), 3.55 (dd, 1H, J=3.5, 9.0 Hz), 3.68 (dd, 1H, J=2.0, 3.5 Hz), 4.53 (d, 1H, J=1.5 Hz). $^{13}$C {1H} NMR (D$_2$O) δ 43.61, 55.30, 69.98, 72.01, 72.40, 102.81. HRMS calculated for C$_7$H$_5$N$_1$O$_5$Na$^+$ (M+Na$^+$) 216.0848, found 216.0853.

Cbz-Thr(α-tetraacetyl-Man)-Val-OMe (Compound 16)

To a solution of 2,3,4,6-triacetyl-D-mannopyranosyl bromide (2.40 g, 5.84 mmol) in dry dichloromethane (30 mL) was added at −20° C. Cbz-Thr-Val-OMe (2.00 g, 5.67 mmol) and silver triflate 92.92 g, 11.4 mmol). The suspension was stirred at −20° C. for 4 hours, and then filtered through a bed of Celite. The filtrate was washed twice with water and twice with saturated sodium bicarbonate. The organic layer was dried over anhydrous MgSO$_4$ and concentrated in vacuo, and the residue was chromatographed with silica gel (eluted with EtOAc/Hexanes=2/1) to give Compound 16 as a white solid (2.8 g, 72 percent yield). $^1$H NMR (500 MHz, CDCl$_3$) δ 0.86 (dd, 6H, J=4.5, 7.0 Hz), 1.20 (d, 3H, J=1.0 Hz), 1.91 (s, 3H), 1.98 (s, 3H), 2.01 (s, 3H), 2.02 (s, 3H), 2.12 (m, 1H), 3.67 (s, 3H), 4.05–4.07 (m, 2H), 4.18–4.20 (m, 1H), 4.33 (t, 2H, J=3.5 Hz), 4.44–4.45 (m, 1H), 5.00 (s, 1H), 5.08 (s, 2H), 5.16–5.24 (m, 3H), 5.81 (d, 1H, NH, J=7.5 Hz), 6.82 (d, 1H, NH, J=8.5 Hz), 7.25–7.32 (m, 5H). $^{13}$C {1H} NMR (CDCl$_3$) δ 16.53, 17.74, 18.71, 20.40, 20.53, 20.58, 30.65, 51.82, 57.31, 58.15, 62.35, 66.69, 67.10, 68.78, 68.83, 69.05, 76.18, 98.85, 127.40, 128.40, 135.81, 156.12, 168.71, 169.40, 170.43, 171.75. HRMS calculated for C$_{32}$H$_{44}$N$_2$O$_{15}$Cs$^+$ (M+Cs$^+$) 829.1796, found 829.1796.

Cbs-Thr(α-Man)-Val-OMe (Compound 7)

To a solution of Cbz-Thr(α-tetraacetyl-Man)-Val-OMe (Compound 16) (200 mg, 0.28 mmol) in 20 mL of dry methanol at zero degrees C. was added 1 percent MeONa in dry methanol (about 500 mL) until pH 10.0. The solution was stirred at zero degrees C. for 1.5 hours. Then Dowex H$^+$ was added to the reaction to pH 4.0. After filtration, the solvent was removed in vacuo to give Compound 7 as a colorless liquid (132 mg, 87 percent yield). $^1$H NMR (500 MHz, D$_2$O) δ 0.85 (dd, 6H, J=4.0, 7.0 Hz), 1.21 (d, 3H, J=6.5 Hz), 2.04–2.07 (m, 1H), 3.26–3.54 (m, 2H), 3.62 (s, 3H), 3.64–3.68 (m, 2H), 3.69–3.74 (m, 2H), 4.10 (m, 1H), 4.24–4.29 (m, 2H), 5.02 (s, 2H), 7.19 (d, 1H, NH, J=3.0 Hz), 7.20–7.28 (m, 5H), 8.10 (d, 1H, NH, J=8.5 Hz). $^{13}$C {1H} NMR (D$_2$O) δ 18.52, 18.91, 19.36, 31.70, 48.66, 48.82, 49.00, 49.17, 49.33, 52.61, 59.19, 60.45, 62.80, 67.83, 68.50, 71.94, 72.26, 74.89, 77.13, 103.01, 128.82, 128.98, 129.41, 137.92, 158.50, 172.58, 173.26. HRMS calculated for C$_{24}$H$_{36}$N$_2$O$_{11}$Cs$^+$ (M+Cs$^+$) 661.1373, found 661.1392.

Thr(α-Man)-Val-OMe (Compound 8)

Hydrogenolysis of Cbz-Thr(α-Man)-Val-OMe Compound 7 (156 mg) in 10 mL methanol in the presence of trifluoroacetic acid (30 mL) and Pd/C produced Compound 8 (130 mg, 87 percent yield). $^1$H NMR (500 MHz, D$_2$O) δ 0.72 (dd, 6H, J=2.5, 7.0 Hz), 1.22 (d, 3H, J=6.5 Hz), 2.00 (m, 1H), 3.40 (t, 1H, J=4.5 Hz), 3.48–3.52 (m, 2H), 3.55 (s, 3H), 3.64 (m, 2H), 3.91 (d, 1H, J=4.0 Hz), 4.68 (d, 1H, J=1.5 Hz). 13C {1H} NMR (D$_2$O) δ 17.42, 17.97, 18.27, 30.00, 52.95, 57.13, 58.86, 61.09, 66.83, 70.04, 70.43, 73.49, 75.25, 101.75, 167.96, 173.56. HRMS calculated for C$_{16}$H$_{30}$N$_2$O$_9$Cs$^+$ (M+Cs$^+$) 527.1006, found 527.1016.

Cbz-Thr(α-Man)-Val-Gly-Ala-NH$_2$ (Compound 9)

Compound 7 (20 mg, 0.038 mmol), Gly-Ala-NH$_2$ (60 mg, 0.24 mmol) and 3.0 mg of subtilisin 8397 in 2.0 mL of 7:3 mixture of dimethylformamide (DMF) and water (pH 8.5–9.0, adjusted with triethylamine) was incubated at room temperature for 2.5 hours. After removing the solvents, the glycopeptide, Compound 9, (12 mg, 43 percent) was isolated by HPLC. $^1$H NMR (500 MHz, CD$_3$OD) δ 0.87 (d, 3H, J=3.0 Hz), 1.18 (d, 3H, J=6.0 Hz), 1.28 (d, 3H, J=7.0 Hz), 1.97 (m, 1H), 3.21 (q, 1H, J=1.5 Hz), 3.51 (m, 2H), 3.61–3.64 (m, 3H), 3.74 (m, 1H), 3.83 (d, 2H, J=3.5 Hz), 4.02 (d, 1H, J=7.0 Hz), 4.20 (s, 2H), 5.02 (s, 3H), 7.20–7.31 (m, 5H). $^{13}$C NMR (D$_2$O) δ 16.81, 17.84, 17.90, 30.51, 35.91, 49.40, 54.20, 59.30, 59.84, 61.10, 67.00, 67.62, 70.41, 70.51, 73.30, 76.10, 101.40, 115.60, 127.80, 128.30, 128.60, 129.01, 130.7, 136.50, 154.60, 172.20, 172.41, 174.48, 174.84. HRMS calculated for $C_{28}H_{43}N_5O_{12}Cs^+$ (M+Cs$^+$) 774.1963, found 774.1958.

Boc-Try-Thr(α-Man)-Val-OMe (Compound 10)

To a solution of 104 mg of Boc-Tyr(Bzl)-OH, 167 mg of H-Thr(α-tetraacetyl-Man)-Val-OMe (synthesized from hydrogenolysis of Compound 14), 50 mL of triethylamine and 44 mg of 1-hydroxybenzotriazole in 2 mL of dry methylene chloride at zero degrees C. were added 63 mg of 1-(3-dimethylaminopropyl)-3-ethylcarbodiimide hydrochloride. The reaction was stirred at zero degrees C. for 12 hours. The mixture was then evaporated to dryness under reduced pressure. Purification by a silica gel column with hexane/EtOAc (1/2, v/v) afforded 138 mg (65 percent yield) of Boc-Tyr(Bzl)-Thr(α-tetraacetyl-Man)-Val-OMe. This compound was then subjected to deacylation and hydrogenolysis as described for the preparation of Compounds 7 and 8 to give Compound 10 in 82 percent overall yield. $^1$H NMR (500 MHz, CD$_3$OD) δ 0.85 (dd, 6H, J=1.5, 7.0 Hz, Val 2CH$_3$), 1.15 (d, 3H, J=6.5 Hz, Thr CH$_3$), 1.28 (s, 9H, Boc), 2.05 (m, 1H, Val CH), 2.64 (dd, 1H, J=9.5, 13.5 Hz, Tyr CH$_2$Ph), 3.20 (m, 1H), 3.51 (m, 2H), 3.59 (dd, 2H, J=5.0, 9.0 Hz), 3.63 (s, 3H, Val OCH$_3$), 3.68 (m, 1H), 3.71 (d, 1H, J=2.5 Hz), 3.73 (d, 1H, J=1.5 Hz), 4.11 (dd, 1H, J=4.0, 6.5 Hz), 4.20 (t, 1H, J=4.5 Hz), 4.23 (d, 1H, J=6.5 Hz), 4.45 (d, 1H, J=4.0 Hz, Man C1-H), 6.58 (d, 2H, J=8.5 Hz, Tyr Ph), 6.95 (d, 2H, J=8.0 Hz, Tyr Ph). $^{13}$C {$^1$H} NMR (CD$_3$OD) δ 18.56, 18.71, 19.41, 28.69, 31.79, 38.07, 52.65, 57.66, 58.13, 59.24, 62.92, 68.67, 72.01, 72.33, 75.01, 76.76, 103.02, 116.23, 129.23, 131.36, 157.28, 171.78, 173.36, 174.79. HRMS calculated for $C_{30}H_{47}N_3O_{13}Cs^+$ (M+Cs$^+$) 790.2163, found 790.2153.

Manα1,2ManαOMe (Compound 3)

A reaction mixture (100 mL, 100 mM Tris, pH 7.5, 10 mM MgCl$_2$, 10 mM MnCl$_2$, 5 mM EDTA, 5 mM NaN$_3$, 1 mM ATP, 0.01 mM theophylline and 0.03 mM 2,3-dimercaptopropanol) containing α-methyl-D-mannopyranoside (0.4 g, 20 mM), Man-1-P (about 1.5 g, about 50 mM), PEP (1.0 g, 42.7 mM), GDP (30 mg, 1 mM), dried yeast cells (0.4 g), pyruvate kinase PK (300 U), recombinant α1,2-ManT (1.2 U) and inorganic pyrophosphatase (2 U) was slightly stirred at room temperature for 72 hours, then centrifuged. The supernatant was lyophilized and extracted with methanol. After removal of the methanol, the product was purified by silica gel column chromatography (CHCl$_3$:CH$_3$OH:H$_2$O=6:3:0.5, v/v/v) to afford Manα1,2ManαOMe (Compound 3) (96 mg) in 38 percent overall yield based on consumed α-methyl-D-mannopyranoside. $^1$H NMR (D$_2$O) δ 3.41 (s, 3H), 3.60–3.80 (m, 6H), 3.86 (dd, 1H, J=3.5, 10 Hz), 3.88 (dd, 1H, J=3.5, 10 Hz), 3.90 (d, 1H, d, J=1.5 Hz), 3.92 (d, 1H, J=1 Hz), 3.97 (dd, 1H, J=2, 3.5 Hz), 4.08 (dd, 1H, J=2, 3.5 Hz), 5.02 (d, 1H, d, J=2 Hz), 5.04 (d, 1H, J=2.0 Hz). $^{13}$C {$^1$H} NMR (D$_2$O) δ 54.90, 61.01, 61.24, 66.98, 67.03, 70.02, 70.29, 70.37, 72.63, 73.40, 78.62, 99.40, 102.43. HRMS calculated for $C_{13}H_{24}O_{11}Na^+$ (M+Na$^+$) 379.1216, found 379.1220.

Cbz-Thr(αManα1,2Man)-Val-OMe (Compound 11)

The synthetic procedure was described before. $^1$H NMR (500 MHz, D$_2$O) δ 0.83 (m, 6H), 1.21 (d, 3H, J=4.5 Hz), 2.04 (m, 1H), 3.55–3.62 (m, 15 H), 4.05 (m, 1H), 4.16 (m, 1H), 4.24 (m, 1H), 5.00 (s, 2H), 7.16–7.27 (m, 5H). $^{13}$C {$^1$H} NMR (D$_2$O) δ 17.63, 17.68, 18.41, 30.10, 52.88, 58.68, 61.14, 61.21, 66.91, 67.19, 67.52, 70.03, 70.13, 70.47, 73.30, 76.47, 79.31, 99.84, 102.40, 127.87, 127.92, 128.60, 129.00, 172.82, 173.80. HRMS calculated for $C_{30}H_{46}N_2O_{16}Cs^+$ (M+Cs$^+$) 823.1902, found 823.1928.

The foregoing description and the examples are intended as illustrative and are not to be taken as limiting. Still other variations within the spirit and scope of this invention are possible and will readily present themselves to those skilled in the art.

What is claimed is:

1. An exogenous DNA present in ATCC No. 77379 that encodes a water dispersible α1,2-mannosyltransferase.

2. *E. coli.* ATCC No. 77379.

* * * * *

SEQUENCE LISTING

<160> NUMBER OF SEQ ID NOS: 2

<210> SEQ ID NO 1
<211> LENGTH: 29
<212> TYPE: DNA
<213> ORGANISM: Homo sapiens

<400> SEQUENCE: 1
atatttctag aagaactcag caatatatt                               29

<210> SEQ ID NO 2
<211> LENGTH: 34
<212> TYPE: DNA
<213> ORGANISM: Homo sapiens

<400> SEQUENCE: 2
gcgcgtcgac ttattactca cggaattttt tcca                         34